United States Patent [19]
Rozich

[11] Patent Number: 5,492,624
[45] Date of Patent: Feb. 20, 1996

[54] WASTE TREATMENT PROCESS EMPLOYING OXIDATION

[75] Inventor: Alan F. Rozich, Exton, Pa.

[73] Assignee: Environmental Resources Management, Inc., Exton, Pa.

[21] Appl. No.: 309,556

[22] Filed: Sep. 20, 1994

Related U.S. Application Data

[63] Continuation of Ser. No. 18,801, Feb. 17, 1993, abandoned.

[51] Int. Cl.⁶ ......................................... C02F 3/30
[52] U.S. Cl. .................. 210/605; 210/607; 210/613; 210/625; 210/631; 210/759; 210/903; 210/906
[58] Field of Search ................................. 210/612, 613, 210/622, 623, 627, 631, 758, 759, 763, 903, 906, 605, 607, 625

[56] References Cited

U.S. PATENT DOCUMENTS

| | | |
|---|---|---|
| 4,276,174 | 6/1981 | Breider et al. ........................ 210/613 |
| 4,915,840 | 4/1990 | Rozich ........................................ 210/613 |
| 5,141,646 | 8/1992 | Rozich ........................................ 210/631 |

*Primary Examiner*—Ivars Cintins
*Attorney, Agent, or Firm*—Lerner, David, Littenberg, Krumholz & Mentlik

[57] ABSTRACT

Processes for the treatment of organic waste are disclosed, including feeding the organic waste to an ATAD reactor and subjecting the organic waste to biological digestion in the ATAD reactor in order to produce a biomass and clear decant therein, oxidizing at least a portion of the biomass so as to produce an oxidized effluent therein, and returning the oxidized effluent to the ATAD reactor. Variations on these processes which are disclosed include the removal of nutrients from the clear decant, treating of the organic waste with a mixer prior to feeding it to the ATAD reactor, feeding the waste by a grinder upstream of the mixer, feeding the mixed material initially to an AAD vessel from which methane gas is removed, and then to the ATAD reactor, with or without nutrient removal, the use of solid separation for the effluent from the ATAD reactor, and other such variants.

41 Claims, 3 Drawing Sheets

WASTE TREATMENT PROCESS EMPLOYING OXIDATION

This is a continuation of application Ser. No. 08/018,801 filed Feb. 17, 1993, now abandoned.

FIELD OF THE INVENTION

The present invention relates to treatment of organic waste materials. More particularly, the present invention relates to improved processes for the treatment of sludge and/or solid organic waste.

BACKGROUND OF THE INVENTION

Numerous aerobic processes have been developed over the years for the biological treatment of municipal waste, including both domestic and industrial sewage, for yielding an environmentally acceptable effluent. One of the widely used aerobic processes for such treatment is referred to as the activated sludge process, in which organic matter contained in the municipal wastes is contacted with an oxygen-containing gas in the presence of suspended biologically active organisms under conditions such that the organic material is converted into a form which can be separated from purified water. In these processes, a portion of the insoluble sludge that is formed is recycled to the aerobic zone. Another such process is the trickling filtration method, in which the microorganisms are fixed to a support.

These activated sludge systems and other aerobic processes usually produce a significant net positive production of sludge containing suspended solids, which must then be discarded on a periodic basis. Such biological sludges are difficult to treat, because they have poor dewatering properties and are highly putrescible. Sludge deposition has thus become an important environmental problem.

Numerous processes have been developed for sludge stabilization, one of which has been anaerobic digestion. In anaerobic processes, the organic material present in the sludge is oxidized to by-products such as organic acids, ammonia, and principally methane. Anaerobic digestion, however, has a high cost of operation, and substantial time is required for the digestion process.

Another process for stabilizing activated sludge is referred to as extended aeration, in which the sludge is contacted in an aerobic digestion zone, and the organic material is oxidized over time. Although extended aeration may offer significant advantages over anaerobic digestion, there are problems associated with such processes because of high operating expenses and capital costs.

Among the many variations in processes associated with the aerobic treatment of municipal waste are the following:

U.S. Pat. Nos. 3,547,814 and 3,670,887 disclose the treatment of sewage wherein gross solids are first removed from the sewage by screening and the remaining waste contacted with an oxygen-containing gas and activated sludge. The '814 patent discloses that anaerobic processes have been used to render the sludge non-putrescible and, as noted, require long-term storage. Another suggested technique for treating such sludge involves extended aeration, which increases the degree of auto-oxidation, with a net reduction of such sludge. Unfortunately, the rate of oxidation was generally too low to have a significant effect on net sludge production. Even with extended aeration and an increased degree of auto-oxidation, particularly at the zero net production of sludge level, problems were presented because of large plant size and high operating costs. To reduce size, these patentees thus suggested using an oxygen-rich gas and a high volatile organic material in the sludge. This resulted in a low sludge yield in the overall process.

U.S. Pat. No. 3,356,609 discloses a process for treating municipal waste wherein the initial sewage is clarified, and the effluent is then enriched with a carbon source and contacted with an oxygen-containing gas and activated sludge in a dispersed culture aerobic reactor.

U.S. Pat. No. 4,246,099 discloses a combination of aerobic/anaerobic processes to reduce and stabilize sludge solids in an activated sludge process. In this process, municipal sludge was initially contacted with an oxygen-containing gas under aerobic conditions to partially reduce the biodegradable volatile suspended solids and then anaerobically digested to partially stabilize the sludge. Sludge reduction to less than 40% of the biodegradable volatile suspended solids introduced to the digestion zone was achieved. The concept of thermal aerobic digestion was referred to as autothermal aerobic digestion (ATAD) wherein the digester was operated at elevated temperatures, e.g., from about 45° C.–75° C., or in the thermophilic range.

U.S. Pat. No. 4,026,793 discloses an aerobic digestion process for reducing the solids content in a biodegradable organic sludge by carrying out the digestion in a vessel maintained at a temperature within the range of 38°–46° C.

U.S. Pat. No. 4,652,374 discloses a modified anaerobic fermentation of municipal waste by effecting hydrolysis and acidification of the sewage and then anaerobically digesting the hydrolyzed sewage under conditions for methane generation.

It is also known in a modified extended aeration activated sludge process in combination with autothermal aerobic digestion (ATAD) to use a hydrolytic assist which comprised the treatment of the effluent from the ATAD reactor with acid and subjecting the resulting hydrolyzed effluent to biological digestion in the initial aeration zone, where the sewage was contacted with an oxygen-containing gas and activated sludge. *Proceedings,* 17th Conference on Municipal Sludge Management, HMCRI, Boston, Mass., 1907, pp. 71–77.

As can be seen from the review of substantial prior art pertaining to aerobic processes, including activated sludge processes, many variations have been proposed in an effort to reduce or minimize sludge production and to stabilize excess sludge produced by aerobic processes. All of these processes in one way or another become quite complex and may exhibit high operating costs or capital costs in order to achieve that objective. In most cases, it is extremely difficult to modify these processes in such a way that there is substantial sludge reduction, based on original organic input, let alone achieving sludge elimination. The latter goal is one often sought but seldom achieved and typically requires intervening physical separation processes such as dewatering and subsequent incineration. Removal of organics from waste streams via respiration and conversion into microbial mass and its subsequent conversion to water and carbon dioxide is seldom achieved.

In my prior U.S. Pat. No. 4,915,840, which is expressly incorporated herein by reference, there is disclosed an improvement for sludge reduction in an aerobic process wherein municipal waste containing organic matter is biologically digested by contact with an oxygen-containing gas in the presence of biologically active organisms. The basic process is shown in FIG. 1 of the '840 patent, which is reproduced as FIG. 1 hereof, the disclosure of which, as set forth in the '840 patent from column 4, line 42 through column 7, line 20, is incorporated herein by reference thereto. In particular, the biological digestion of sludges in an autothermal aerobic digestion unit (ATAD) is a known process. In autothermal aerobic digester zone 34, air, or other oxygen-containing gas, e.g., high purity oxygen, is introduced through line 36 at a rate sufficient for the autothermal thermophilic aerobic digestion of the suspended solids. In this process, a temperature of from about 35°–75° C. is maintained, and the heat generated in the process should be sufficient to maintain temperature without external heating. These autothermal self-heating units contain the metabolic heat generated and require no external heat addition to maintain the autothermal digester at appropriate conditions. The nonconverted product containing organic material of preselected concentration usually from 0.5 to 2% solids, is removed as effluent from autothermal aerobic digester zone 34 via line 35 and all or a portion charged to initial aeration digester zone 6. The recycle plus recycle from secondary clarifier 12 is adjusted to give the desired preselected sludge value. With appropriate decay in autothermal digester zone 34, no net sludge generation is possible. That portion not charged to aerobic zone 6 is removed through line 39 for disposal.

It is specifically noted that in the process of the '840 patent, as is shown in FIG. 1 hereof, sludge reduction is controlled by means of a portion of thickened biologically activated sludge being contacted in hydrolysis vessel 31 (HYD) with acid, e.g., sulfuric acid or base, e.g., alkali metal hydroxide under conditions sufficient to effect hydrolysis of macromolecular components of the organic cells and effect dissolution of inorganic components. Mild acid hydrolysis is achieved in vessel 31 by adding acid and maintaining a pH in the range of from about 0.5 to 2 at a pressure ranging from atmospheric to about 30 psig at temperatures ranging from about 80° to 130° C. for about 2 to 10 hours, typically about 4 to 6 hours. Alkaline hydrolysis can also be effected, and this is achieved by contacting with alkaline materials, e.g., sodium hydroxide, and maintaining a pH of from about 7 to 12 and a temperature of 20° to 50° C. for about 5 to 12 hours. This hydrolytic assist modifies the cell structure of the macromolecular components and renders them essentially soluble and thereby enhances the ability of the biologically active organisms to effect thermophilic decay within the autothermal aeration digester zone 34. By increasing or deceasing the amount of the thickened sludge subjected to hydrolysis, one increases or decreases the rate of decay for the system, and sludge reduction levels can be controlled by controlling the rate of such decay, and thus, the extent of decay. However, since the temperature conditions within the ATAD unit itself can effect some solubilization of these macromolecular components, to that extent, the prior chemical solubilization by hydrolytic assist can be considered to be redundant or inefficient.

Hydrolyzed sludge not charged to autothermal aerobic digester zone 34 may be treated for removal of phosphorous or nitrogen or may be adjusted in pH for optimizing decay in the autothermal aerobic digestion zone. Hydrolyzed sludge is withdrawn from vessel 31 through line 38 and charged to tank 40 wherein pH, for example, is adjusted upwardly to an alkaline level for precipitation of phosphorus compounds which are then removed through line 42. The balance of material in vessel 40 is removed through line 44 and charged to autothermal aerobic digester zone 34.

In accordance with a further improved process of mine, as disclosed in U.S. patent application Ser. No. 07/668,070, filed on Mar. 12, 1991, now U.S. Pat. No. 5,141,646, the disclosure of which is incorporated herein by reference thereto, sludge is charged directly to an ATAD reactor from a mixing vessel to provide immediate digestion. During periodic quiescent periods, a portion of settled biomass is then removed from the ATAD reactor and charged to a hydrolysis unit for treatment with a strong acid or base solution. The settled biomass is permitted to hydrolyze for a period of time, preferably at least about six hours, and is then returned to the mixing chamber upstream of the ATAD reactor. The hydrolysate is mixed with the incoming sludge which is then fed directly to the ATAD reactor. The incoming sludge neutralizes the hydrolyzed stream to bring it to a desired pH 7. The hydrolyzed sludge, which is above room temperature, also helps to heat up the incoming feed sludge. Periodically, purified decant is removed from the ATAD reactor and returned to the plant.

A particularly preferred embodiment of the process is shown in FIG. 5 of the '646 patent, and is reproduced in FIG. 2 hereof. In this process, the sludge or solid waste comprising approximately 8% solids may be fed to the grinder 86 via line 84 and thereafter to the mixer 54 via line 52. The sludge is thereafter passed via line 56 to an autothermal anaerobic digestion (AAD) unit 88 where methane gas is drawn off via line 90. Optionally (via line 92), settled biomass from the AAD unit may be hydrolyzed in the unit 62 and recirculated to the mixing chamber 54. If necessary, excess sludge may be removed via line 93 upstream of the hydrolysis vessel 62.

The AAD unit 88 is an autothermal anaerobic digestion device. It is similar to the ATAD reactor 58, except that it requires higher input solids concentration and it is anaerobic, so that no oxygen (aeration) is supplied. The AAD unit is designed to extract energy from the sludge or trash prior to ultimate stabilization via composting. Water and/or nutrients may be added to the AAD unit, if desired, via line 96. AAD decant from unit 88 is fed to the ATAD reactor 58 via line 94.

A portion of the ATAD biomass is settled and removed as before, and returned to the hydrolysis unit 62 via line 60, the hydrolyzed stream feeding into mixer 54 via line 66. Purified decant from the ATAD reactor may be returned to the plant via line 70, or introduced into a nutrient removal device 72, as described above. Treated decant is returned to the plant via line 78.

The search has therefore continued for improved processes for treating organic wastes and sludge materials so as to reduce the generation of sludge and to do so in a more economical and simplified process.

SUMMARY OF THE INVENTION

In accordance with the present invention, these and other objects have now been achieved by the discovery of a process for the treatment of organic waste which includes the steps of feeding the organic waste to an ATAD reactor, and subjecting the organic waste to biological digestion in the ATAD reactor so as to produce a biomass and a clear decant therein, oxidizing at least a portion of the biomass so as to produce an oxidized effluent therein, and returning the oxidized effluent to the ATAD reactor. A particular advantage of utilizing such an oxidizing step as compared to the hydrolysis step of the '840 patent is that in the case of the oxidation step of the present invention, dissolved solids are not produced which can adversely impact on the downstream processing thereof. In the case of hydrolysis, as in the '840 patent, on the other hand, copious amounts of dissolved solids are produced, thus providing a potential basis for adversely effecting various downstream processes. In addition, another advantage as compared to the '840 patent is in the fact that in the process of the present invention, whatever solubilization which can occur by means of elevated temperatures in the ATAD reactor takes place before the chemical oxidation step, and the redundancy or inefficiency in the prior art is avoided hereby.

In a preferred embodiment, the process includes periodically removing the clear decant from the ATAD reactor. Preferably, the process also includes separating solids from the liquor, in the form of the ATAD biomass, and then returning the separated biomass to the ATAD reactor, with the clear decant then being discharged.

In accordance with a preferred embodiment of the process of the present invention, the oxidizing step is a chemical oxidation step. Preferably, the chemically oxidizing step comprises contacting at least a portion of the biomass with hydrogen peroxide in the presence of a Fenton's reagent catalyst, preferably ferrous sulphate.

In accordance with another embodiment of the process of the present invention, the process includes separating at least a portion of the biomass from the clear decant prior to the oxidizing step. Preferably, the oxidizing step is carried out at a pH of between about 1.0 and 6.0, and preferably at about 3.5.

In accordance with a preferred embodiment of the process of the present invention, the organic waste is subjected to biological digestion in the ATAD reactor at a temperature of between about 40° and 70° C., and most preferably at least a portion of the biomass is chemically oxidized at a temperature of at least about 50° and generally between about 50° and 70° C., although higher temperatures are possible. Thus, in addition to the heat generated during biological digestion itself, further heat is generated during the chemical oxidation process. In other words, the heat generated prior to the oxidation step is being used to catalyze further oxidation of the macromolecular components therein, and, in fact, in some cases permits one to eliminate the need for the catalyst discussed above.

In a preferred embodiment, the process includes removing nitrogen and phosphorous from the clear decant to produce a purified clear decant. Preferably the nitrogen is removed biologically, and the phosphorous is removed by precipitation.

In accordance with another embodiment of the process of the present invention, waste treatment is carried out by feeding the waste to an AAD vessel and subjecting the waste to biological digestion in the AAD vessel so as to produce a first biomass and a first decant therein, feeding the first decant from the AAD vessel to an ATAD reactor and subjecting the first decant to biological digestion in the ATAD reactor so as to produce a second biomass and a second decant therein, oxidizing at least a portion of the second biomass so as to produce an oxidized effluent therein, and returning oxidized effluent to the AAD vessel.

Preferably, this process includes separating at least a portion of the second biomass from the second decant prior to the oxidizing step.

In accordance with a preferred embodiment of the process of the present invention, the oxidizing step comprises a chemically oxidizing step, preferably including contacting at least a portion of the second biomass with hydrogen peroxide in the presence of a Fenton's reagent catalyst, preferably ferrous sulphate.

BRIEF DESCRIPTION OF THE DRAWINGS

Other objects and advantages of the present invention will become apparent from an analysis of the following detailed description, which refers to the drawings, in which.

DETAILED DESCRIPTION

Figure 3:
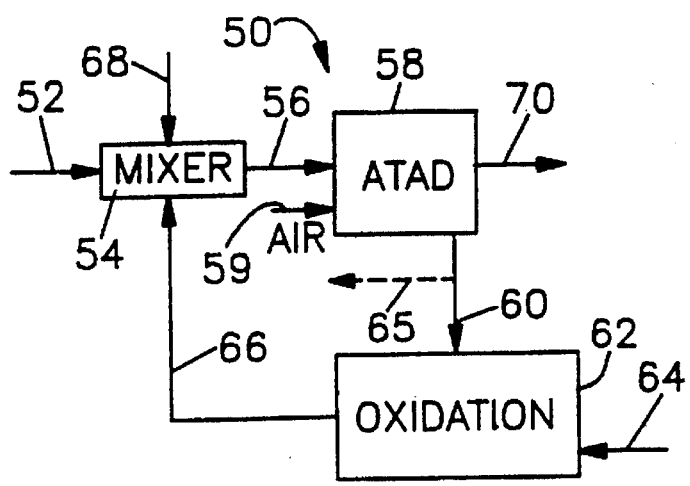
FIG. 3 is a block flow diagram of a waste treatment process employing oxidization in accordance with one embodiment of the present invention.

Referring to the Figures, in which like reference numerals refer to like portions thereof, FIG. 3 shows a system 50 for treatment of sludge in which a sludge comprising at least about 2% solids, but preferably at least about 4% solids is charged through an input line 52 to a mixing vessel 54 and thereafter via line 56 to an ATAD reactor unit 58. The function of the mixer 54 will be described further herein.

Figure 1:
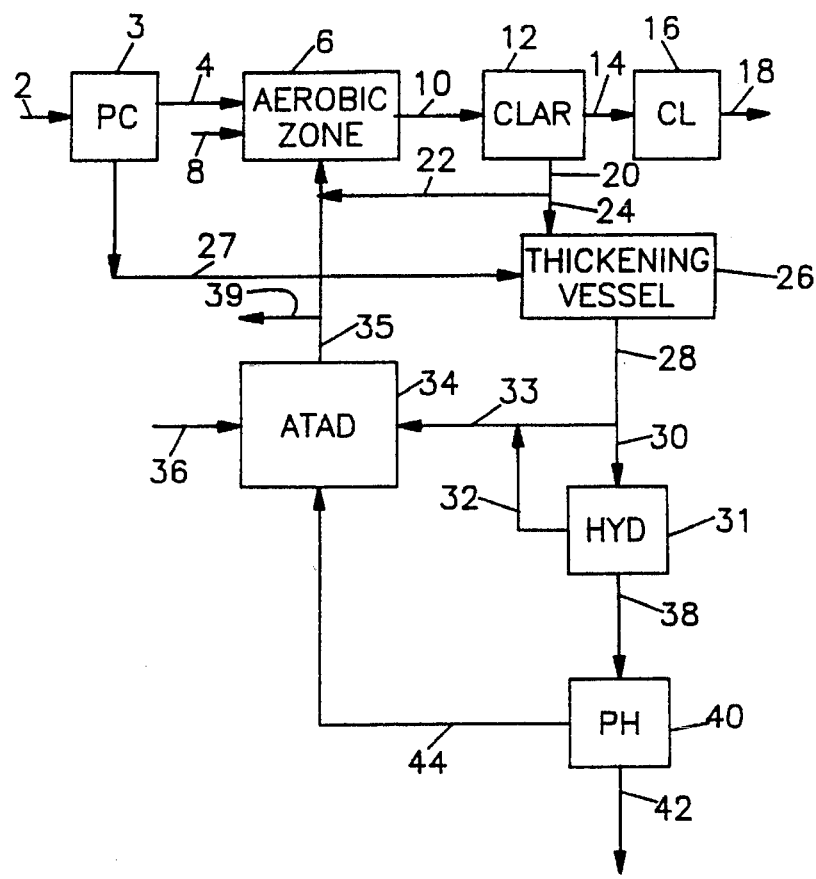
FIG. 1 is a block flow diagram of an activated sludge process incorporating a hydrolytic assist for an autothermal aerobic digestion zone for enhanced sludge reduction as set forth in U.S. Pat. No. 4,915,840.
Figure 2:
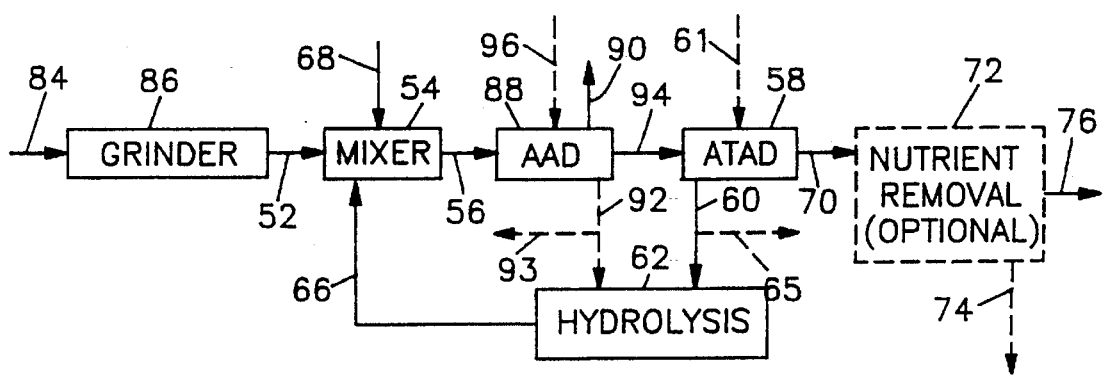
FIG. 2 is a block flow diagram of an activated sludge process in which a portion of the biomass from the ATAD reactor is hydrolyzed-in a hydrolysis vessel and the hydrolyzed effluent is then returned to the input of the ATAD reactor in accordance with U.S. Pat. No. 5,141,646.

In the ATAD reactor unit 58, an autothermal thermophilic aerobic digestion process as described in the '814 patent is effected at about 40°–70° C. The ATAD reactor unit 58 is shown in FIGS. 1 and 2 hereof, which are discussed hereinabove and constitute the prior art as shown in the '840 patent. In particular, in operation of this unit, the unconverted product containing organic material of preselected concentration, usually from 0.5 to 2% solids, is removed as effluent from autothermal aerobic digester zone 34 via line 35. Air or other oxygen-containing gas, or in some cases nitrates, are introduced via line 59 into the ATAD reactor 58 at the appropriate rate for the aerobic digestion of the suspended solids in the reactor. Periodically, for example, once daily, the ATAD reactor unit 58 is shut down and the biomass within the reactor is allowed to settle during a quiescent period (preferably about ½ to 1 hour). Thereafter, a portion of the settled biomass, and preferably between 1% and about 10% of the ATAD reactor biomass, is withdrawn from the ATAD unit 58 and is charged via line 60 to the oxidation vessel 62 for oxidative treatment therein.

In the oxidation vessel 62, chemical oxidation preferably takes place. This is preferably accomplished by using hydrogen peroxide as the chemical oxidant. Oxidation of the ATAD reactor biomass is preferably carried out in a batch stirred reactor in which the pH is maintained constant at a level of between about 1 and 6, and preferably at a pH of about 3.5, this being accomplished by the addition of acid, such as sulfuric acid, in an amount as may be required to do so. The oxidation reaction can be catalyzed by the use of Fenton's reagent, i.e., ferrous sulphate, which can be periodically added to the reactor. The amount of ferrous sulphate added, of course, depends upon the throughput of the reactor, but generally will be an amount of up to about 100 mg. per liter and, when such a catalyst is utilized, preferably between about 3 and 100 mg. per liter, and most preferably between about 5 and 10 mg. per liter. As discussed above, however, where the temperature of the biomass is high enough, in some cases it is possible to effect an autocatalytic reaction without the need to add this catalyst thereto. It is also possible, however, to employ other well-known chemical oxidation processes, such as ozonization, in which ozone is generated electrically and then introduced as the oxidizing agent; chemical oxidation utilizing agents, such as dichromates and permanganates; and wet air oxidation, at elevated temperatures and pressures, all of which are commercial processes, known as heat treatment processes, such as the Zimpro and Porteus process.

In the oxidation vessel 62 itself, various chemical components are oxidized. Most particularly, among the various organic components thereof, various toxic components of the settled biomass stream can be oxidized, including components which are not amenable to processes such as the hydrolysis of the '646 patent. These include complex hydrocarbons or highly reduced hydrocarbons such as PCB's, etc. The elimination of these toxic materials is not only important on an overall basis, but doing so also helps to increase the efficiency of the ATAD reactor itself (as well as the AAD reactor in accordance with the embodiment discussed below). Furthermore the oxidation of recalcitrant or potentially inhibiting organic materials allows the process to function more efficiently, primarily because the accumulation of target toxic components in the ATAD or AAD reactor is thereby prevented.

Furthermore, in connection with hydrolysis reactions employing either strong acid or base, the possibility of side reactions exists which might, in turn, create additional toxic components. This potential is also eliminated by use of the oxidative treatment of the present invention. In these oxidation reactions, it is therefore possible to break down such toxic components to their most basic components, so as to produce carbon dioxide therefrom. This, of course, is impossible using hydrolysis reactions.

Therefore, by utilizing the oxidation treatment of the present invention, there is a substantial reduction in the chemical oxygen demand (COD) of the organic material, thus improving the efficiency and lowering the overall oxidation demand in the ATAD reactor. This provides yet another benefit both in terms of the nature of the product attained therefrom, and in terms of financial savings.

On a overall basis, the present invention thus both reduces the COD as well as solubilizing significant portions of the chemical components contained in the settled biomass being treated therein. In any event, the oxidized effluent from the oxidation reactor 62 is then introduced via line 66 to the mixing vessel 54 where it mixes with the incoming feed sludge from line 52. In this way, the incoming feed sludge also neutralizes the oxidized stream, bringing it closer to the desired pH. If needed, however, further pH adjustment can be effected by addition of an acid or base via line 68.

It will also be appreciated that the oxidized sludge added to the mixer 54 is warm, thereby helping to raise the temperature of the incoming sludge from feedline 52, and thereby further reducing cost by eliminating or at least reducing the need for separate heating equipment.

Periodically, a purified clear decant is removed from the ATAD unit 58 and returned to the plant via line 70. The ATAD effluent may also be conveyed to a solids separator (such as a clarifier, thickener or ultrafilter) for the purpose of separating the ATAD biomass from the decant. Some of the separated ATAD biomass may then be conveyed back to the ATAD reactor, while another portion may be sent to the oxidation unit (see FIG. 7). This separation of the ATAD biomass is particularly significant where the product is intended to be subjected to any further downstream aerobic biological treatment. The presence of any significant portion of the thermophilic (ATAD) biomass therein can have a serious negative impact thereon. More particularly, this ATAD biomass is rather recalcitrant, and resists degradation in such downstream biological treatment systems. This, in turn, results in a significant build-up of this material in these downstream systems, thus hindering the overall performance of these processes.

It is also noted that it is preferred that the sludge charged to mixing vessel 54 has about a 4% solids content. However, lower solids contents, such as down to about 2% solids, can also be treated in some cases, such as where the heat generated in the biological reactions in the ATAD reactor is sufficient to operate thermophilically.

Figure 4:
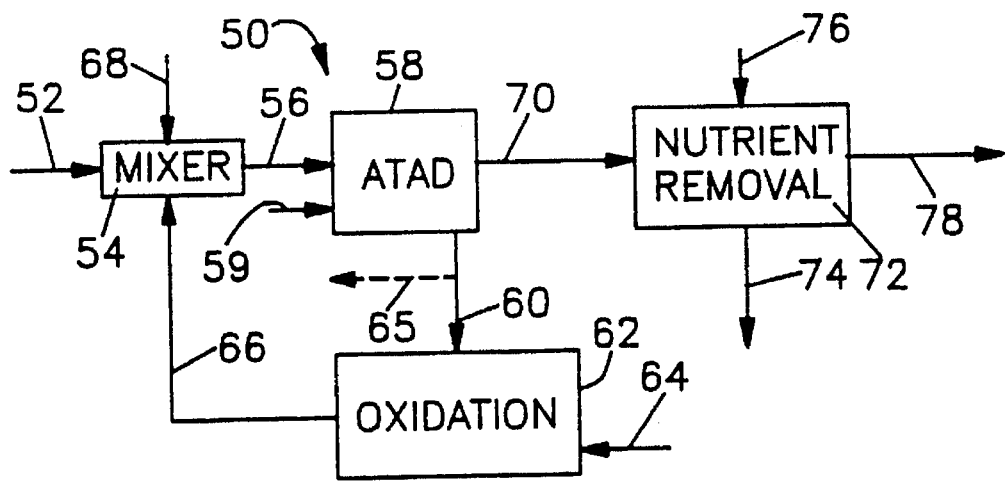
FIG. 4 is a block flow diagram of another waste treatment process in accordance with the present invention.

Referring next to FIG. 4, there is illustrated another embodiment of the invention which is similar to the embodiment described hereinabove relative to FIG. 3, but which enables the removal of nutrients from the decant line 70. Specifically, FIG. 4 illustrates a nutrient removal station 92 which receives purified decant from the line 70, and is treated to remove nitrogen and phosphorous. In this embodiment, chemicals are added via line 76 to the nutrient removal station 72 while phosphate/chemical sludge is either recycled to the oxidation reactor 62 and/or removed via line 74. The treated decant is then returned to the plant via line 78.

In this embodiment, the phosphorous is preferably removed from the decant by precipitation, while nitrogen is preferably removed biologically or by other suitable means, such as by air stripping of ammonia. Heretofore, it had not been recognized that nitrogen and additional phosphorous would be produced in an ATAD reactor during digestion. Thus, the suggested mode of nutrient removal in my earlier '840 patent is inefficient by comparison. It will be appreciated that nutrient removal will also remove other dissolved solids which may pose a problem in other downstream treatment processes.

Figure 5:
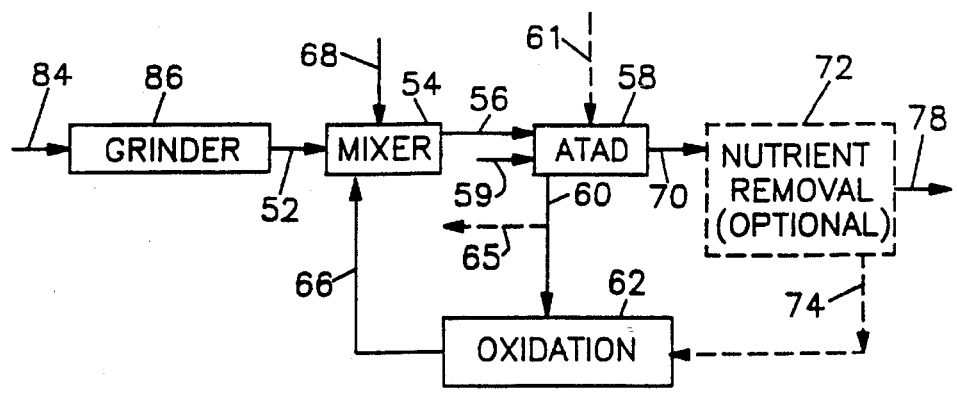
FIG. 5 is a block flow diagram of yet another waste treatment process in accordance with the present invention.

With reference to FIG. 5, a third embodiment of the invention is disclosed for the treatment of solid organic wastes. In this embodiment, an arrangement similar to that shown in FIG. 4 is utilized, with the addition of a grinder upstream of the mixer 54. Specifically, a trash stream comprising at least 4% solids is introduced via a line 84 into a grinder 86 which is operatively connected via line 52 to the mixer 54. The grinder is utilized in this embodiment to reduce particle size and to convert the solids to a more amenable state for biodegradation via liquid composting. Thus, this system is appropriate for treatment of trash, garbage, leaves, grass clippings and so on. As a further feature of this embodiment, water and/or nutrients may be added to the ATAD reactor 58 via line 61 if desired.

A significant advantage of the above-described arrangement is that since nutrients may need to be added for some types of solid organic wastes, using the above-described method where the ATAD biomass is oxidized, allows nutrients to be recycled to the process via mixer 54, thereby conserving chemical usage.

The nutrient removal step described above with respect to FIG. 5 may also be employed. If desired, the final preferred product may then be returned to the plant via line 78.

Figure 6:
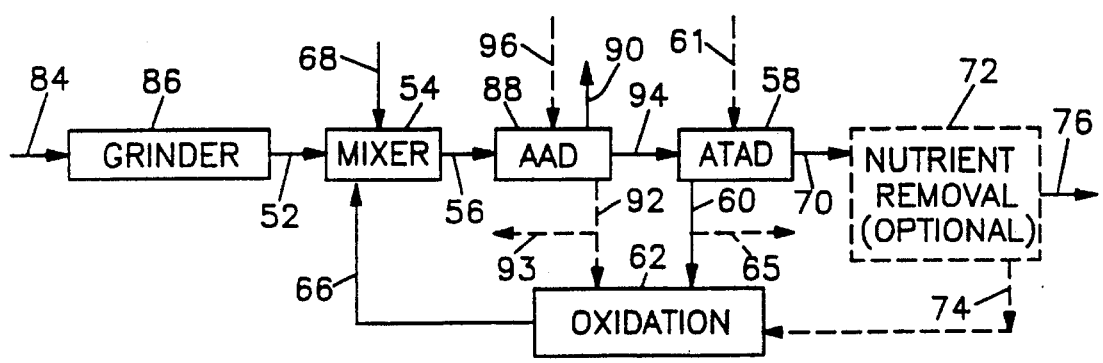
FIG. 6 is a block flow diagram of yet another embodiment of a waste treatment process in accordance with the present invention.

In FIG. 6, another embodiment of the invention is disclosed in the context of an energy generation system which extracts methane gas from sludge/trash prior to composting.

In this embodiment, the sludge or solid waste comprising approximately 8% solids may be fed to the grinder 86 via line 84 and thereafter to the mixer 54 via line 52. The sludge is thereafter passed via line 56 to an autothermal anaerobic digestion (AAD) unit 88 where methane gas is drawn off via line 90. Optionally, through line 92, settled biomass from the AAD unit may be oxidized in the oxidation reactor 62 and then recirculated to the mixing chamber 54. If necessary, excess sludge can be removed through line 93 of the oxidation reactor 62.

The AAD unit 88 is an autothermal anaerobic digestion device. It is similar to the ATAD reactor 58, except that it requires higher input solids concentration and it is anaerobic, so that no oxygen (aeration) is supplied. The AAD unit is designed to extract energy from the sludge or trash prior to ultimate stabilization via composting. Water and/or nutrients may be added to the AAD unit, if desired, via line 96. AAD decant from unit 88 is fed to the ATAD reactor 58 via line 94.

A portion of the ATAD biomass is settled and removed as before, and returned to the oxidation reactor 62 through line 60, the oxidized stream therefrom passing to the mixer 54 through line 66. Purified decant from the ATAD reactor can be returned to the plant through line 70, or it can be introduced into a nutrient removal device 72, as described above. Treated decant can be returned to the plant through line 76.

Figure 7:
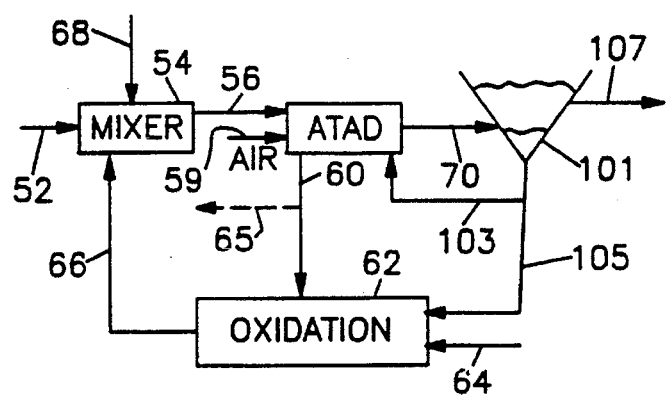
FIG. 7 is a block flow diagram of another waste treatment process in accordance win the present invention.

Referring next to FIG. 7, in another embodiment of the present invention, similar to that shown in FIG. 3, a solid separation step is employed with respect to the decant removed through decant line 70. Specifically, FIG. 7 illustrates a solid separator 101, such as a clarifier, thickener or ultrafilter, from which solids, such as the ATAD biomass contained in the decant stream, are separated from the decant and either recycled to the ATAD reactor through line 103, and/or recycled to the oxidation reactor 62 through line 105. The purified decant can then be returned to the plant through line 107. In all other respects, the components of FIG. 7 are the same as those shown in FIG. 3 and discussed above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A process for the treatment of organic waste comprising the steps of:
   (a) feeding said organic waste to an ATAD reactor and subjecting said organic waste to biological digestion in said ATAD reactor, so as to convert at least a portion of said organic waste therein and produce a biomass containing unconverted organic material and a clear decant therein;
   (b) contacting at least a portion of said biomass with a chemical oxidation agent, so that said chemical oxidation agent is solely responsible for the oxidation of said unconverted organic material from said ATAD reactor and produce an oxidized effluent therein; and
   (c) returning said oxidized effluent to said ATAD reactor.

2. The process of claim 1, including periodically removing said clear decant from said ATAD reactor.

3. The process of claim 1 wherein said contacting step comprises contacting said at least a portion of said biomass with a chemical oxidation agent comprising hydrogen peroxide in the presence of a Fenton's reagent catalyst.

4. The process of claim 3 wherein said Fenton's reagent catalyst comprises ferrous sulphate.

5. The process of claim 1 including separating said at least a portion of said biomass from said clear decant prior to said oxidizing step.

6. The process of claim 1 wherein said contacting step is carried out at a pH of between about 1 and 6.

7. The process of claim 6 wherein said contacting step is carried out at a pH of about 3.5.

8. The process of claim 1 wherein said organic waste comprises at least 2% solids.

9. The process of claim 1 wherein said organic waste comprises at least 4% solids.

10. The process of claim 1 comprising subjecting said organic waste to biological digestion in said ATAD reactor at a temperature of between about 40° and 70° C.

11. The process of claim 10 comprising contacting said at least a portion of said biomass at a temperature of between about 40° and 70° C.

12. The process of claim 1 including removing nitrogen and phosphorous from said clear decant to produce a purified clear decant.

13. The process of claim 12 including removing said nitrogen biologically.

14. The process of claim 12 including removing said phosphorous by precipitation.

15. The process of claim 12 including recycling at least a portion of said purified clear decant to said contacting step.

16. The process of claim 1 including mixing said organic waste upstream of said ATAD reactor.

17. A process for treatment of waste comprising the steps of:
   (a) feeding said waste to an AAD vessel and subjecting said waste to biological digestion in said AAD vessel so as to produce a first biomass and a first decant therein;
   (b) feeding said first decant from said AAD vessel to an ATAD reactor and subjecting said first decant to biological digestion in said ATAD reactor so as to convert at least a portion of said organic waste therein and produce a second biomass containing unconverted organic material and second decant therein;
   (c) contacting at least a portion of said second biomass with a chemical oxidation agent, so that said chemical oxidation agent is solely responsible for the oxidation of said unconverted organic material from said ATAD reactor and produce an oxidized effluent therein; and
   (d) returning said oxidized effluent to said AAD vessel.

18. The process of claim 17 including separating out at least a portion of said second biomass from said second decant prior to said contacting step.

19. The process of claim 18 including removing nitrogen and phosphorous from said second decant to produce a purified clear decant.

20. The process of claim 17 wherein said contacting step comprises contacting at least a portion of said second biomass with a chemical oxidation agent comprising hydrogen peroxide in the presence of a Fenton's reagent catalyst.

21. The process of claim 20 wherein said Fenton's reagent catalyst comprises ferrous sulphate.

22. The process of claim 17 wherein said contacting step is carried out at a pH of between about 1 and 6.

23. The process of claim 22 wherein said contacting step is carried out at a pH of 3.5.

24. The process of claim 17 wherein the input waste comprises at least 8% solids.

25. The process of claim 17 including separating said first biomass from said AAD vessel and charging said separated portion of said first biomass to said contacting step.

26. The process of claim 17 including mixing said waste upstream of said AAD vessel.

27. The process of claim 26 including grinding the solid waste upstream of said mixing step.

28. The process of claim 17 including adding water or nutrients to said AAD vessel.

29. The process of claim 17 including adding water or nutrients to said ATAD reactor.

30. A process for the treatment of organic waste comprising the steps of:
   (a) feeding said organic waste to an ATAD reactor and subjecting said organic waste to biological digestion in said ATAD reactor, so as to convert at least a portion of said organic waste therein and produce a biomass containing unconverted organic material and a clear decant therein;
   (b) chemically oxidizing at least a portion of said biomass by means of a chemical oxidation process selected from the group consisting of treatment with hydrogen peroxide, ozonization, treatment with dichromates or permanganates, and wet air oxidation at elevated temperatures and pressures, so as to oxidize at least a portion of said unconverted organic material from said ATAD reactor and produce an oxidized effluent therein; and
   (c) returning said oxidized effluent to said ATAD reactor.

31. The process of claim 30 wherein said oxidizing step comprises contacting said at least a portion of said biomass with a chemical oxidation agent comprising hydrogen peroxide.

32. The process of claim 31 wherein said oxidizing step comprises contacting said at least a portion of said biomass with a chemical oxidation agent comprising hydrogen peroxide in the presence of a Fenton's reagent catalyst.

33. The process of claim 30 including separating said at least a portion of said biomass from said clear decant prior to said oxidizing step.

34. The process of claim 30 wherein said oxidizing step is carried out at a pH of between about 1 and 6.

35. The process of claim 34 wherein said oxidizing step is carried out at a pH of about 3.5.

36. The process of claim 30 comprising oxidizing said at least a portion of said biomass at a temperature of between about 40°–70° C.

37. A process for the treatment of organic waste comprising the steps of:
   (a) feeding said organic waste to an ATAD reactor and subjecting said organic waste to biological digestion in said ATAD reactor so as to convert at least a portion of said organic waste therein and produce a biomass containing unconverted organic material and a clear decant therein;
   (b) non-biologically oxidizing at least a portion of said biomass so as to produce an oxidized effluent therein;
   (c) returning said oxidized effluent to said ATAD reactor.

38. The process of claim 37, including separating out at least a portion of said biomass from said clear decant prior to said oxidizing step.

39. The process of claim 38, including removing nitrogen and phosphorous from said clear decant to produce a purified clear decant.

40. The process of claim 39, including removing said nitrogen biologically.

41. The process of claim 39, including removing said phosphorous by precipitation.

* * * * *